United States Patent [19]
Guazzi

[11] Patent Number: 6,040,445
[45] Date of Patent: Mar. 21, 2000

[54] ACYCLOVIR DIHYDRATE SODIUM SALT AND THE PREPARATION THEREOF

[75] Inventor: Giuseppe Guazzi, Cassino D'Alberi Mulazzano, Italy

[73] Assignee: Solchem Italiana S.p.A., Assago, Italy

[21] Appl. No.: 08/957,847

[22] Filed: Oct. 27, 1997

[30] Foreign Application Priority Data

Feb. 21, 1997 [IT] Italy .................................. MI97A0383

[51] Int. Cl.⁷ ................................................. C07D 473/18
[52] U.S. Cl. ............................................................ 544/276
[58] Field of Search ............................................. 544/276

[56] References Cited

U.S. PATENT DOCUMENTS

| | | | |
|---|---|---|---|
| 3,819,620 | 6/1974 | Dursch | 260/243 C |
| 4,504,657 | 3/1985 | Bouzard | 544/30 |
| 4,562,181 | 12/1985 | Crisp | 514/202 |

OTHER PUBLICATIONS

Physicians Desk Reference, 51st edition, p. 1067, 1997.
European Pharmacopoeia, p. 387, 1997.
Physicians Desk Reference #1 Entry for Zovirax Acyclivor Sodium, 1996.
Physician Desk Reference #2 Entries for Prinivil and Vasotec, 1996.
American Drug Index p. 350, 1976
Aspe, Journal Phar. Sci 84, p. 750, Jun. 1995

*Primary Examiner*—Mark L. Berch
*Attorney, Agent, or Firm*—Walter H. Schneider

[57] ABSTRACT

9-[(2-Hydroxyethoxy)methyl]guanine (acyclovir) dihydrate sodium salt and the process for the preparation thereof comprising the dissolution of acyclovir monosodium salt in an aqueous medium and the precipitation of the resultant dihydrate sodium salt in an organic solvent.

2 Claims, 1 Drawing Sheet

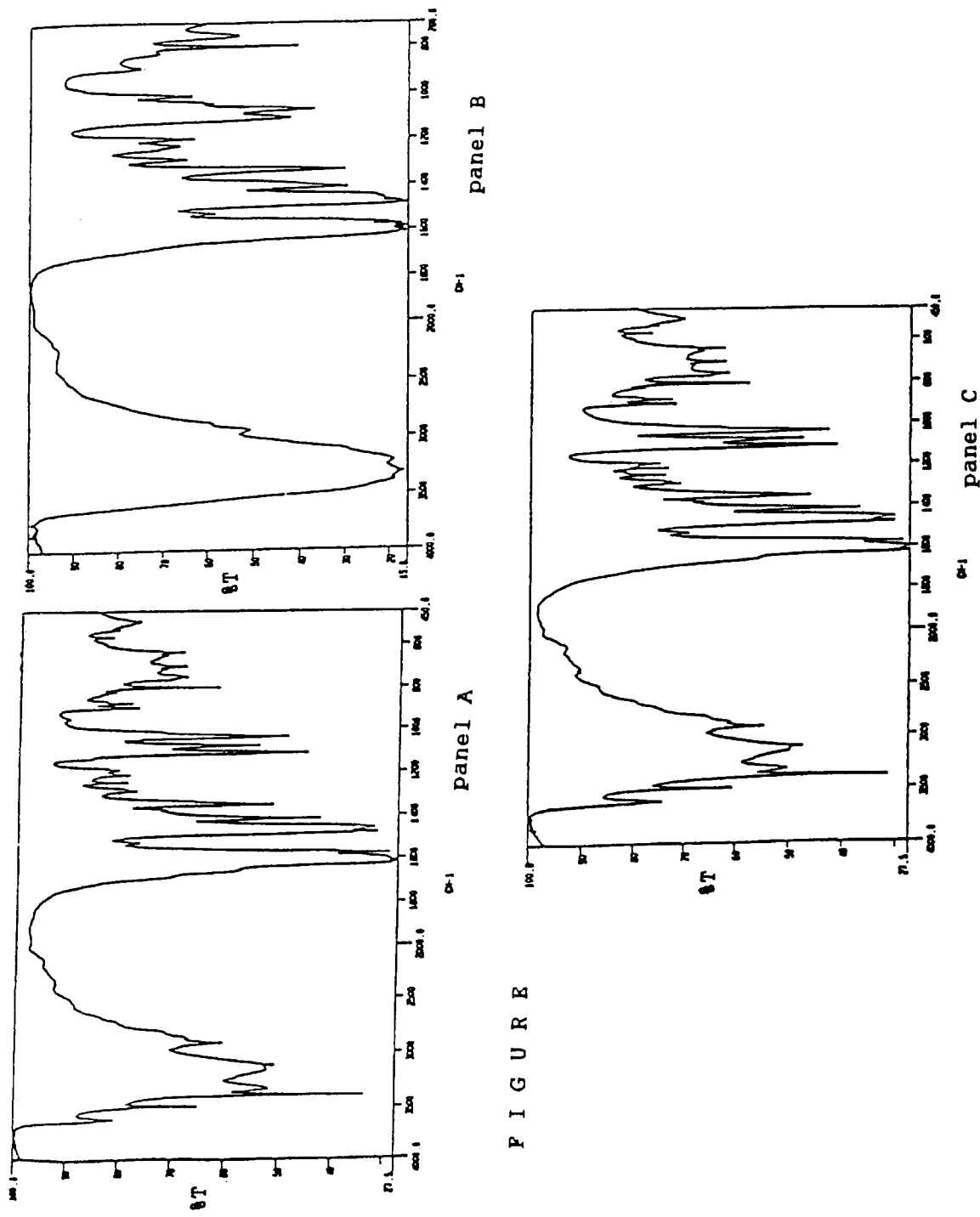
FIGURE

ACYCLOVIR DIHYDRATE SODIUM SALT AND THE PREPARATION THEREOF

The present invention relates to 9-[(2-hydroxyethoxy)methyl]guanine (acyclovir) dihydrate sodium salt of the formula

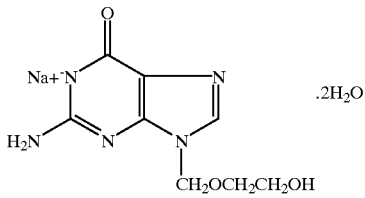

and to a process for the preparation thereof.

Acyclovir is a nucleoside analogue with the glucide substituent open and it is particularly known as an antiviral agent used in the treatment of diseases due to Herpes genitalis, Herpes simplex, Herpes zoster and Epstein-Barr.

Acyclovir can be prepared according to different processes, as reported in BP 1,523,965, U.S. Pat. No. 4,199,574, U.S. Pat. No. 4,146,715, U.S. Pat. No. 4,554,634, U.S. Pat. No. 5,223,619 e U.S. Pat. No. 5,496,945. The cited documents neither disclose acyclovir dihydrate sodium salt, nor the method for the preparation thereof.

Acyclovir dihydrate sodium salt according to the present invention can be prepared according to a process comprising the dissolution of acyclovir monosodium salt in solvents such as methanol, ethanol, water or in mixtures of water with isopropanol, ethanol, methanol, acetone, dimethylformamide, dimethylacetamide, and the subsequent precipitation of the dihydrate sodium salt from a solvent selected from isopropanol, ethanol, methanol, acetone, dimethylformamide and dimethylacetamide.

The process leads to the precipitation of a product having a water content from 11 to 15% by weight, corresponding to 2 water molecules per acyclovir sodium salt molecule, with melting point of about 120° C.

A preferred embodiment of the present invention allows to prepare acyclovir dihydrate sodium salt in apyrogenic and sterile conditions, after a suitable filtration of the aqueous solution before crystallization.

The dihydrate sodium salt is the crystalline stable form into which acyclovir sodium salt spontaneously transforms by adsorption of water molecules after exposure to the environment humidity, as evidenced by the comparison of the IR spectra obtained from samples of the freeze-dried product, of the same freeze-dried product after exposure to air and of the dihydrate sodium salt according to the present invention (see Fig.): the spectra of the latter two samples are in fact superimposable and correspond to the crystalline structure. Moreover, the product resulting from freeze-drying an acyclovir sodium salt aqueous solution, by exposure to the environment humidity, hydrates to a water content of 11–15% by weight, corresponding to a crystal dihydrate form.

Acyclovir dihydrate sodium salt of the present invention can suitably be formulated with appropriate excipients according to conventional techniques, such as those described in Remington's Pharmaceutical Sciences Handbook, Mack. Pub., N.Y., U.S.A.; 17th Ed., 1985; particularly preferred are the formulations suitable for the injectable, oral and topical preparations.

The following examples further illustrate the invention.

EXAMPLE 1

Acyclovir (90 g; 0.376 moles) is suspended in distilled water (480 ml) in a 1 liter glass round-bottomed flask. A solution of sodium hydroxide (15.9 g; 0.397 moles) in distilled water (100 ml) is dropped therein at a temperature of 20° C. Decolourizing charcoal (0.8 g) is added, and the solution is filtered, washing the filter with distilled water. The resulting solution is dropped slowly into a 5 liter glass round-bottomed flask containing acetone previously cooled at a temperature of 10° C. (2800 ml). The mixture is kept under stirring for some hours, after which the resulting crystalline white product is filtered with suction. The filtration cake is washed with cold acetone.

The product is recovered and dried under vacuum at a temperature of 40–45° C. for 16 hours.

83 g of product having 12.45% K.F. are obtained.

EXAMPLE 2

A sodium hydroxide 29% w/w solution (29.8 g; 0.209 moles) is dropped into a 500 ml glass round-bottomed flask containing a suspension of Acyclovir (50 g; 0.209 moles) in distilled water (75 ml). The resulting solution is filtered through fluted filter paper and dropped into a 2 l glass round-bottomed flask containing isopropanol previously cooled at 0–5° C. (850 ml). After some hours under stirring, the resulting crystalline product is filtered and the filtration cake is washed with cold isopropanol, then dried under vacuum at 50° C. for 16 hours.

58.2 g of a crystalline white product having 13% K.F. are obtained.

The Examples 3 and 4 show the interconversion between the forms freeze-dried Acyclovir sodium salt and Acyclovir crystalline dihydrate sodium salt.

EXAMPLE 3

Sodium hydroxide (3.36 g; 0.084 moles) is dissolved in distilled water (50 ml) in a 250 ml glass round-bottomed flask. Acyclovir 2/3 $H_2O$ (20 g; 0.084 moles) is added and the resulting solution is concentrated to dryness to obtain a residue, which is taken up with methanol (100 ml) and stirred at room temperature for some hours. The resulting crystalline solid is filtered and washed with some methanol.

The residue is recovered and dried under vacuum at a temperature of 55° C. for 16 hours.

16.5 g of a crystalline white product having 1.8% are K.F. obtained.

A sample of the same product, after exposure to air for 8 hours, shows a 13.5% water content.

EXAMPLE 4

Acyclovir (200 g; 0.844 moles) is suspended in distilled water (300 ml) in a 1 liter glass flask and a sodium hydroxide 30% w/w solution (83.5 ml) is dropped therein to obtain complete dissolution at pH 12.5, measured at a temperature of 22° C. The solution is dropped into cold isopropanol (3200 ml) and the resulting solid crystalline product is recovered and dried. 217 g of crystalline sodium salt having 13.6% K.F. are obtained.

20 g of said product are redissolved in distilled water (150 ml) and distributed into vials, each containing 12 ml of the obtained solution. Said vials are freeze-dried.

13 Vials of freeze-dried acyclovir sodium salt, each of about 1.3 g, are thereby obtained.

The water content of one of said vials, determined immediately after opening, is 2.6%. The same sample of freeze-dried product, after exposure to air for 60 min. shows a 14.8% water content (stable even after 8 hours).

EXAMPLE 5

Preparation of Crystalline Apyrogenic Acyclovir Dihydrate Sodium Salt

Dry acyclovir (K.F. 5%) (40 kg) and demineralized water (60 l) are placed into a 250 l stainless steel reactor. A sodium hydroxide 30% aqueous solution (25.3 kg) is dropped therein with stirring until complete dissolution, at a temperature of 20° C.

Said solution is filtered through a millipore 0.22 μm filter in an enameled reactor (800 l) containing isopropanol (700 l), keeping stirring for some hours, then centrifuging the resulting crystalline white product. The product is then washed with isopropanol, recovered and dried at a temperature of 60° C. for 16 hours under vacuum.

About 44 kg of crystalline apyrogenic acyclovir dihydrate sodium salt (L.A.L. Test<0.167 E.U./mg) are obtained.

I claim:

1. A process for the preparation of the dihydrate sodium salt of Acyclovir which comprises dissolving Acyclovir and sodium hydroxide in a solvent selected from water or a mixture of water with isopropanol, ethanol, methanol, acetone, dimethylformamide or dimethylacetamide, and precipitating the resulting dihydrate sodium salt in a solvent selected from isopropanol, ethanol, methanol, acetone, dimethylformamide and dimethylacetamide.

2. A process according to claim 1, wherein the dihydrate sodium salt of is prepared in sterile, apyrogenic conditions.

* * * * *